US009364649B2

(12) United States Patent
Park et al.

(10) Patent No.: US 9,364,649 B2
(45) Date of Patent: Jun. 14, 2016

(54) CONTAINER FOR SKIN CARE WITH HEATING MASSAGE FUNCTION

(71) Applicant: AMOREPACIFIC CORPORATION, Seoul (KR)

(72) Inventors: Wooram Park, Seoul (KR); So-hee Kim, Seoul (KR); Yoonhee Lee, Seoul (KR); Cheonghwan Hwang, Seoul (KR); Hyesung Nam, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/373,882

(22) PCT Filed: Feb. 1, 2013

(86) PCT No.: PCT/KR2013/000824
§ 371 (c)(1),
(2) Date: Jul. 22, 2014

(87) PCT Pub. No.: WO2013/115591
PCT Pub. Date: Aug. 8, 2013

(65) Prior Publication Data
US 2015/0038926 A1 Feb. 5, 2015

(30) Foreign Application Priority Data

Feb. 2, 2012 (KR) .................... 20-2012-0000819

(51) Int. Cl.
*A46B 11/02* (2006.01)
*A46B 13/04* (2006.01)
(Continued)

(52) U.S. Cl.
CPC ............. *A61M 35/003* (2013.01); *A45D 34/04* (2013.01); *A61F 7/007* (2013.01); *A61H 9/00* (2013.01);
(Continued)

(58) Field of Classification Search
CPC ................ A61F 2007/0078; A61M 35/003; A46B 11/02; G01F 11/00; B05B 11/00
USPC ................... 401/188 R, 152; 251/61
See application file for complete search history.

(56) References Cited

U.S. PATENT DOCUMENTS 5,037,007 A * 8/1991 Deussen ............... G01F 11/021
222/321.6
5,700,991 A * 12/1997 Osbern .................. H05B 3/00
219/214

(Continued)

FOREIGN PATENT DOCUMENTS

JP 2000-140060 A 5/2000
KR 10-0286989 4/2001

(Continued)

*Primary Examiner* — Mark A Laurenzi
*Assistant Examiner* — Thomas M Abebe
(74) *Attorney, Agent, or Firm* — East West Law Group; Heedong Chae

(57) ABSTRACT

A skin cosmetic container includes an opening/closing unit capable of discharging contents introduced into a cylinder provided within a first body in which the contents are stored to the outside of the first body as a pressure is applied to a push button provided on a pump body mounted to an upper portion of the first, body and including a discharge hole for discharging the contents flowing along a guide passage in the pump body to the outside of the first body to selectively open and close a content passage, the skin cosmetic container including: a second body mounted to a lower portion of the first body and having a temperature controller therein; a power source mounted within the second body; and a heater mounted to an end of the second body to emit heat by using electric power applied from the power source and including a heat emitting portion whose heat emitting temperature is controlled by the temperature controller.

4 Claims, 3 Drawing Sheets

(51) Int. Cl.
  *A46B 11/04* (2006.01)
  *G01F 11/00* (2006.01)
  *A61M 35/00* (2006.01)
  *A61F 7/00* (2006.01)
  *A61H 9/00* (2006.01)
  *A45D 34/04* (2006.01)

(52) U.S. Cl.
  CPC ..... *A45D 2200/055* (2013.01); *A45D 2200/056* (2013.01); *A45D 2200/155* (2013.01); *A61F 2007/0052* (2013.01); *A61F 2007/0078* (2013.01); *A61F 2007/0087* (2013.01)

(56) References Cited

U.S. PATENT DOCUMENTS

| | | | | |
|---|---|---|---|---|
| 5,979,711 | A * | 11/1999 | Fuchs | B05B 11/0005 222/321.2 |
| 6,216,911 | B1 * | 4/2001 | Kreitemier | A45D 34/00 222/1 |
| 7,011,467 | B1 * | 3/2006 | Fiore | A46B 11/0055 401/188 R |
| 7,431,181 | B2 * | 10/2008 | Masuda | B05B 11/007 222/256 |
| 7,828,177 | B2 * | 11/2010 | Decottignies | B05B 11/007 222/321.7 |
| 2005/0129453 | A1 * | 6/2005 | Bravo-Loubriel | A46B 5/0091 401/188 R |
| 2006/0263140 | A1 * | 11/2006 | Tani | A45D 40/04 401/55 |
| 2007/0041779 | A1 * | 2/2007 | Kuo | A46B 11/0058 401/188 R |
| 2008/0314934 | A1 * | 12/2008 | Decottignies | B05B 11/007 222/321.3 |
| 2009/0123213 | A1 * | 5/2009 | Tani | A45D 40/04 401/75 |
| 2009/0290929 | A1 * | 11/2009 | Rolion | B43K 24/084 401/109 |
| 2012/0170967 | A1 * | 7/2012 | Faison | A46B 9/04 401/135 |

FOREIGN PATENT DOCUMENTS

| | | |
|---|---|---|
| KR | 10-0746214 B1 | 8/2007 |
| KR | 10-2011-0066722 A | 6/2011 |
| KR | 10-1050069 B1 | 7/2011 |

* cited by examiner

CONTAINER FOR SKIN CARE WITH HEATING MASSAGE FUNCTION

BACKGROUND OF THE INVENTION

1. Field of the Invention

The present invention relates to a skin cosmetic container, and more particularly to a airless skin cosmetic container having a heat emitting massage function, in which a heating massage function is implemented at a lower portion of the skin cosmetic container to allow a a portion of skin on which a skin cosmetic material is applied to be smoothly massaged.

2. Description of the Related Art

In general, massage is known to help heal insomnia, depression, or want of sleep, and alleviate stresses and fatigues and pains of muscles. The massages were started by massagers who had studied massage professionally, and are currently performed by using massaging machines variously released according to parts of bodies and purposes.

Examples of such massaging machines are disclosed in Korean Patent No. 10-0458150 (hereinafter, Prior Document 1) and Korean Unexamined Patent Application No. 2001-0017128 (hereinafter, Prior Document 2). The invention disclosed in Prior Document 1 relates to a unit body for a heating device which can be realized through a simple manufacturing process and cannot easily breakdown, and a heating device for a heating treating machine using the same. The unit body for a heating device includes a body in which various parts are installed and including a support, a heat supply plate positioned on the support to generate high temperature heat by using external electric energy, a heating/fomenting member located on an upper surface of the heat supply plate, for receiving the high temperature heat of the heat supply plate and supplying the heat to the body of a user to perform a heating/fomenting function, and a cover having a support hole for supporting the heating/fomenting member therein and coupled to the body. However, the machine disclosed in Prior Document 1 is inconvenient to carry, is not easy to control temperature with, and may cause a burn during use.

Meanwhile, in the apparatus disclosed in Prior Document 2, In order to improve a massaging machine according to the related art, a heat conducting plate and a ceramic pad are attached to one side surface of a semiconductor heat exchanging device, a cooling water tank is attached to an opposite side surface thereof, a power pole converting switch circuit is connected to a power input line of the semiconductor heat exchanging device in parallel, an electric pole converting program circuit output is connected to the power pole converting switch, and an inrush current limiting device is connected to a power input of the semiconductor heat exchanging device in series, a power ON/OFF relay switch is connected, and an electric pole converting program circuit output, a plus temperature upper limit control circuit, and a minus temperature upper limit control circuit are connected to a power ON/OFF relay switch.

However, the apparatus disclosed in Prior Document 2 is inconvenient to carry and use, and it inconvenient to effectively apply a massage oil or a cosmetic material on skin

BRIEF SUMMARY OF THE INVENTION

The present invention provides a skin cosmetic container having a heating massage function which has a small size and a simple configuration to provide a space in which a skin cosmetic material can be accommodated while being carried conveniently, making it possible to conveniently use oil.

In accordance with an aspect of the present invention, there is provided a skin cosmetic container including an opening/closing unit capable of discharging contents introduced into a cylinder provided within a first body in which the contents are stored to the outside of the first body as a pressure is applied to a push button provided on a pump body mounted to an upper portion of the first body and including a discharge hole for discharging the contents flowing along a guide passage in the pump body to the outside of the first body to selectively open and close a content passage, the skin cosmetic container including: a second body mounted to a lower portion of the first body and having a temperature controller therein; a power source mounted within the second body; and a heater mounted to an end of the second body to emit heat by using electric power applied from the power source and including a heat emitting portion whose heat emitting temperature is controlled by the temperature controller.

The heater may include: a heating coil for emitting heat by using electric power applied from the power source; a coil support mounted to the second body to support the heating coil; and a skin contact formed to cover the heating coil so as to transfer heat emitted from the heating coil to skin.

The skin contact may be formed of a metal or a thermally conductive resin.

According to the present invention, a skin cosmetic container having a heating massage function has a small size and a simple configuration to provide a space in which a skin cosmetic material can be accommodated while being carried conveniently, making it possible to conveniently use oil.

BRIEF DESCRIPTION OF THE DRAWING

The objects, features and advantages of the present invention will be more apparent from the following detailed description in conjunction with the accompanying drawings, in which.

DETAILED DESCRIPTION OF THE INVENTION

The above-mentioned and other objects, and new features of the present invention will be clearer through the specification and the accompanying drawings.

Hereinafter, a skin cosmetic container having a heating massage function according to an exemplary embodiment of the present invention will be described in detail with reference to the accompanying drawings.

Figure 1:
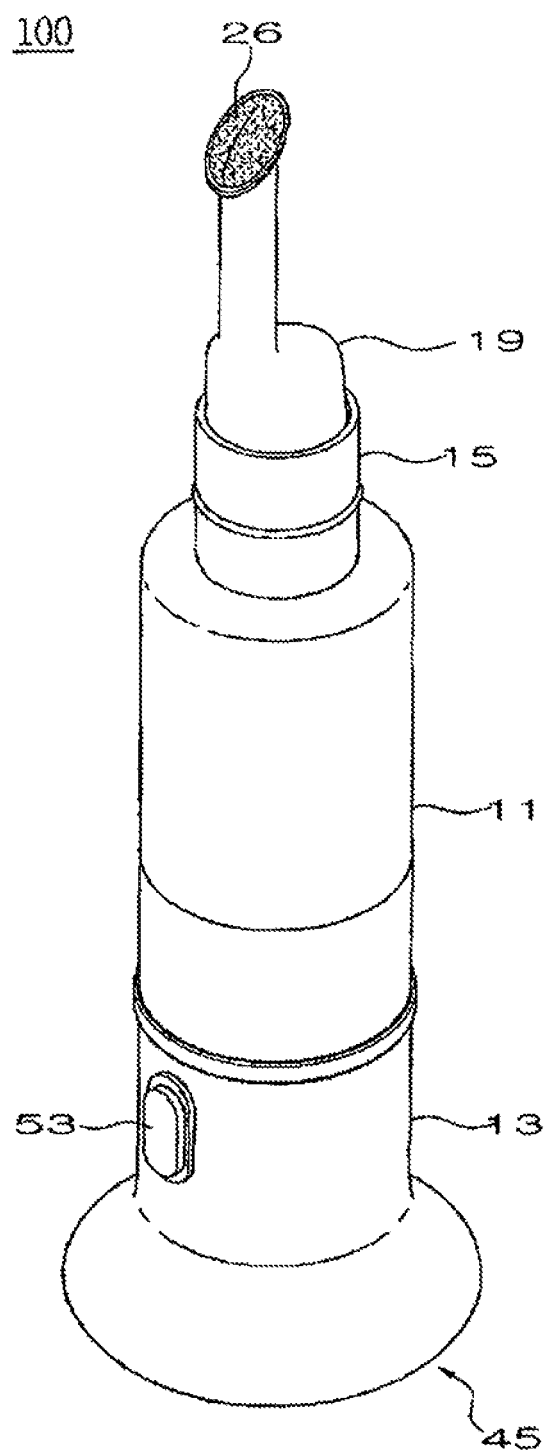
FIG. 1 is a perspective view showing a skin cosmetic container having a heating massage function according to the embodiment of the present invention.
Figure 2:
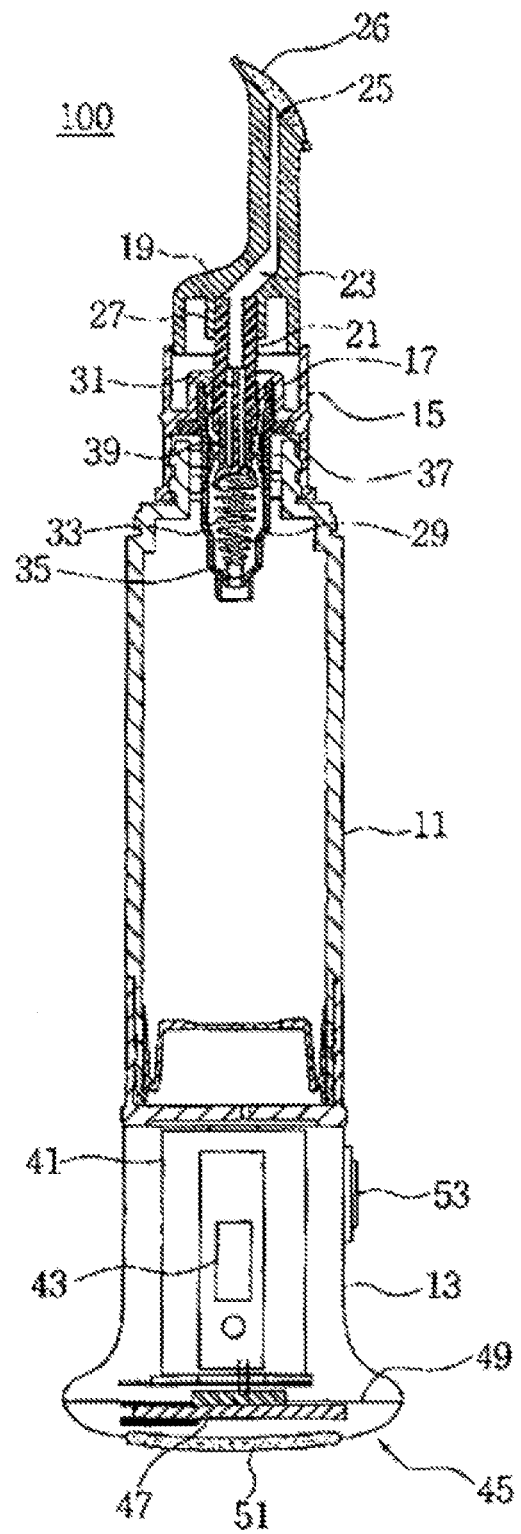
FIG. 2 is a view showing a section of the skin cosmetic container having a heating massage function according to the embodiment of the present invention.
Figure 3:
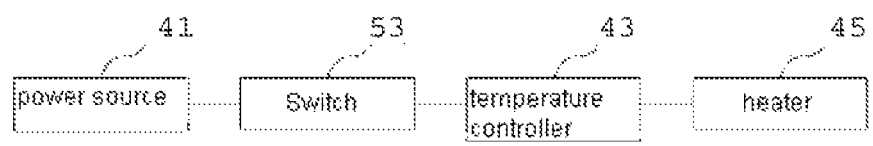
FIG. 3 is a view schematically showing a heating massage unit employed in the skin cosmetic container according to the embodiment of the present invention.

FIG. 1 is a perspective view showing a skin cosmetic container having a heating massage function according to the embodiment of the present invention. FIG. 2 is a view showing a section of the skin cosmetic container having a heating massage function according to the embodiment of the present invention. FIG. 3 is a view schematically showing a heating massage unit employed in the skin cosmetic container according to the embodiment of the present invention.

Referring to FIGS. 1 and 2, the skin cosmetic container 100 of the present invention includes a first body 11, and a second body 13 mounted to a lower portion of the first body 11. The first body 11 includes a storage space for storing contents, for example, a liquefied or gel cosmetic material. A pump body 15 for discharging the contents to an upper portion of the first body 11 is mounted to an upper portion of the first body 11. A fixing guide 17 integrally formed with a pump body 15 is located o an inner wall of the pump body 15.

A push button 19 is located on the pump body 15. The push button 19 has a discharge hole 25 for discharging the contents flowing along a guide passage 23 of a guide tube 21 located within the pump body 15 to the outside of the container, a discharging pad 26 for discharging the contents to the outside of the container. The discharging pad 26 is mounted on top of the discharge hole 25. The push button 19 has a protrusion 27 protruding from a bottom surface of the push button 19 and surrounding a portion of the guide passage 23. Thus, the contents may be discharged to the outside of the first body 11 through the discharge hole 25 by applying a pressure to the push button 19.

The guide tube 21 is connected to a lower portion of the push button 19 such that the guide passage 23 and the discharge hole 25 are communicated with each other. The guide tube 21 is vertically moved in a cylinder 29 located within the pump body 15. The guide tube 21 is preferably vertically moved within the cylinder 29 according to a pressure applied to the push button 19. When a pressure is applied to the push button 19, the contents stored in the cylinder 29 is discharged through the discharge hole 25.

The cylinder 29 is mounted to the fixing guide 17 to be located within the pump body 15. The cylinder 29 is preferably fitted with and fixed to the fixing guide 17. The cylinder 29 becomes narrower as it goes toward an end of the cylinder 29 located within the container. A guide piston 31, a first resilient unit 33, and an opening/closing unit 35 are located within the cylinder 29.

A portion of the guide piston 31 is located within the guide tube 21 within the cylinder 29. The guide piston 31 is preferably moved in the same way as the guide tube 21. The guide piston 31 controls the first resilient unit 33 for operating the opening/closing unit 35 located in a lower interior of the cylinder 29 by a pressure applied by the push button 19. The first resilient unit 33 is interposed between the guide piston 31, and the opening/closing unit 35 located inside an end of the cylinder 29. The first resilient unit 33 is preferably a spring. The opening/closing unit is preferably formed in a ball type.

Another portion of the guide piston 31, that is, the guide piston 31 located outside the guide tube 21 is surrounded by a closed piston 37. The closed piston 37 serves to prevent the contents of the container from being leaked to the outside of the cylinder 29. An outer side of the closed piston 37 is surrounded by the second resilient unit 39. When a pressure is applied to the push button 19, the second resilient unit 39 is compressed by an end of the guide tube 21 located within the cylinder 29. The second resilient unit 39 is preferably formed with a spring having a resilient force different from that of the first resilient unit 33.

Referring to FIGS. 2 and 3, an accommodation space is formed in the second body 13 mounted to the skin cosmetic container 100 of the present invention, and a power source 41, an temperature controller 43, and a heater 45 are positioned in the accommodation space. The power source 41 may be a general primary or secondary battery. The temperature controller 43 controls a temperature of the heater 45 by using a variable resistance, a bimetal, a regulator or the like The heater 45 is mounted to an end of the second body 13 to emit heat by using electric power applied from the power source 41. The heater 45 includes a heating coil 47 for emitting heat by using electric power applied from the power source 41, a coil support 49 mounted to the second body 13 to support the heating coil 47, and a skin contact 51 formed to cover the heating coil 47 so as to transfer heat emitted from the heating coil 47 to skin. The heating coil 47 is disposed in various ways, that is, in zigzags or circularly to uniformly transfer heat to the skin contact 51.

The skin contact 51 may be formed of a thermally conductive metal or alloy, for example, iron, stainless steel, or an alloy thereof, aluminum or an alloy thereof, copper, silver, gold, or an alloy thereof, may be formed by mixing a thermally conductive resin, for example, a silicon resin with a filling material such as thermally conductive carbon fibers, or may be formed by mixing a silicon resin with aluminum, aluminum oxide, boron nitride, aluminum nitride, magnesium oxide, silicon carbon, conductive carbon black, or copper powder which has an excellent thermal conductivity. A switch 53 for controlling an ON/OFF state of electric power applied to the heating coil 47 is provided at an outer side of the second body 13. Thus, according to the skin cosmetic container 100, a temperature of the heating coil 47 can be rapidly raised according to a request of the user or a temperature of the heating coil 47 can be controlled to massage a desired portion of skin.

Although an embodiment of the present invention has been described in detail, the present invention is not limited thereto but may be variously modified without departing from the spirit of the present invention.

What is claimed is:

1. A skin cosmetic container comprising an opening/closing unit capable of discharging contents introduced into a cylinder provided within a first body in which the contents are stored to the outside of the first body as a pressure is applied to a push button provided on a pump body mounted to an upper portion of the first body, a discharge hole for discharging the contents flowing along a guide passage in the pump body to the outside of the first body to selectively open and close a content passage, and including a discharging pad for discharging the contents to the outside of the container wherein the discharging pad is mounted on top of the discharge hole, the skin cosmetic container comprising:

a first resilient unit interposed between a guide piston and the opening/closing unit located inside an end of a cylinder;
  a second resilient unit which surrounds an outer side of a closed piston;
  a second body mounted to a lower portion of the first body and having a temperature controller therein;
  a power source mounted within the second body; and
  a heater mounted to an end of the second body to emit heat by using electric power applied from the power source and including a heat emitting portion whose heat emitting temperature is controlled by the temperature controller, wherein the second resilient unit has a resilient force different from that of the first resilient unit.

2. The skin cosmetic container of claim 1, wherein the heater comprises:

a heating coil for emitting heat by using electric power applied from the power source;
  a coil support mounted to the second body to support the heating coil; and
  a skin contact formed to cover the heating coil so as to transfer heat emitted from the heating coil to skin.

3. The skin cosmetic container of claim 2, wherein the skin contact is formed of a metal or a thermally conductive resin.

4. The skin cosmetic container of claim 1, wherein the first resilient unit is formed with a spring and the second resilient unit is formed with a spring.

* * * * *